United States Patent
Salinas Andrade

(10) Patent No.: US 9,492,374 B2
(45) Date of Patent: Nov. 15, 2016

(54) COMPOSITION AND METHOD FOR TREATMENT OF ULCERS

(71) Applicant: Jose Rafael Salinas Andrade, Managua (NI)

(72) Inventor: Jose Rafael Salinas Andrade, Managua (NI)

( * ) Notice: Subject to any disclaimer, the term of this patent is extended or adjusted under 35 U.S.C. 154(b) by 0 days.

(21) Appl. No.: 14/668,930

(22) Filed: Mar. 25, 2015

(65) Prior Publication Data

US 2016/0279053 A1 Sep. 29, 2016

(51) Int. Cl.
| | |
|---|---|
| A61K 38/14 | (2006.01) |
| A61K 31/7036 | (2006.01) |
| A61K 31/4196 | (2006.01) |
| A61K 31/496 | (2006.01) |
| A61K 31/4164 | (2006.01) |
| A61P 17/02 | (2006.01) |
| A61K 9/00 | (2006.01) |
| A61K 47/02 | (2006.01) |

(52) U.S. Cl.
CPC .......... A61K 9/0014 (2013.01); A61K 31/4164 (2013.01); A61K 31/4196 (2013.01); A61K 31/496 (2013.01); A61K 31/7036 (2013.01); A61K 38/14 (2013.01); A61K 47/02 (2013.01)

(58) Field of Classification Search
CPC ............... A61K 9/0014; A61K 38/14; A61K 31/7036; A61K 31/4196; A61K 31/496; A61K 31/4164; A61K 47/02
See application file for complete search history.

(56) References Cited

U.S. PATENT DOCUMENTS

| | | | |
|---|---|---|---|
| 4,073,694 | A | 2/1978 | Buda et al. |
| 5,707,653 | A | 1/1998 | Goldberg |
| 5,773,000 | A | 6/1998 | Bostwick et al. |
| 6,191,143 | B1 | 2/2001 | Watts et al. |
| 6,344,181 | B2 | 2/2002 | Boykin, Jr. |
| 7,030,093 | B2 | 4/2006 | Vogt et al. |
| 7,241,746 | B2 | 7/2007 | Wingrove et al. |
| 7,264,825 | B2 | 9/2007 | Vogt et al. |
| 7,517,528 | B2 | 4/2009 | Wong et al. |
| 7,691,862 | B2 | 4/2010 | Wingrove et al. |
| 8,211,909 | B2 | 7/2012 | Hsu et al. |
| 8,389,021 | B2 * | 3/2013 | Baker ................. A61K 9/0014 424/629 |
| 2001/0047035 | A1 | 11/2001 | Boykin et al. |
| 2001/0048915 | A1 | 12/2001 | Boykin, Jr. |
| 2003/0119783 | A1 * | 6/2003 | Chang ................. A61K 9/0014 514/58 |
| 2003/0130225 | A1 * | 7/2003 | Ahmad ................ A61K 9/0034 514/45 |
| 2003/0212104 | A1 | 11/2003 | Tracey et al. |
| 2007/0264304 | A1 | 11/2007 | Kuhn et al. |
| 2009/0124632 | A1 * | 5/2009 | Babapour ............ A61K 31/496 514/253.08 |
| 2012/0177757 | A1 | 7/2012 | Hidmi et al. |
| 2013/0045269 | A1 * | 2/2013 | Dovlatabadi ........ A61K 36/185 424/445 |

OTHER PUBLICATIONS

Frank et al, Approach to infected skin ulcers, Can Fam Physician, 2005, 51, pp. 1352-1359.*
Albaugh et al, The Effect of a Cellulose Dressing and Topical Vancomycin on Methicillin-resistant *Staphylacoccus aureus* (MRSA) and Gram-positive Organisms in Chronic Wounds: A Case Series, Ostomy Wound Management, 2013, 59, pp. 34-43.*
Lee et al, Effects of gentamicin solution and cream on the healing of open wounds, Am J Vet Res, 1984, 45, pp. 1487-1492.*
Baroni et al, Topical amikacin formulation induces fibroblast growth factor and cytokine release from human dermal fibroblasts, Arch Dermatol Res, 1999, 291, pp. 296-299.*
Girish et al, The influence of some azoles on wound healing in albino rats, Indian J Pharmacol, 2005, 37, pp. 247-250.*
Holloway, Recognising and treating the causes of chronic malodorous wounds, Nursing Times, 2004, pp. 1-8.*
Duimel-Peeters et al, A Systematic Review of the Efficacy of Topical Skin Application of Dimethyl Sulfoxide on Wound Healing and as an Anti-Inflammatory Drug, Wounds, 2003, 15, pp. 361-370.*
Alexander et al, Updated Recommendations for Control of Surgical Site Infections, Ann Surg, 2011, 253, pp. 1082-1093.*
Mangete et al, Hypertonic Saline Solution: An Effective Wound Dressing Solution, East African Medical Journal, 1993, 70, pp. 104-106.*
Liu et al, Fibroblast proliferation due to exposure to a platelet concentrate in vitro is pH dependent, Wound Rep Reg, 2002, 10, pp. 336-340.*
Runeman et al, Experimental Candida albicans Lesions in Healthy Humans: Dependence on Skin pH, Acta Derm Venereol, 2000, 80, pp. 421-424.*
Stewart et al, *Staphylococcus aureus* Growth Boundaries: Moving towards Mechanistic Predictive Models Based on Solute-Specific Effects, Applied and Environmental Microbiology, 2002, 68, pp. 1864-1871.*
Yosipovitch et al, Skin Surface pH: A Protective Acid Mantle, Cosmetics & Toiletries magazine, 1996, 111, pp. 1-2.*
Wilson et al, The pH of varicose ulcer surfaces and its relationship to healing, VASA, 1979, pp. 339-342.*

* cited by examiner

*Primary Examiner* — Julie Ha
*Assistant Examiner* — Li Ni Komatsu
(74) *Attorney, Agent, or Firm* — Hector M. Reyes Rivera

(57) ABSTRACT

There is provided pharmaceutical compositions suitable for the treatment of infected ulcers in mammals, such as diabetes related ulcers and varicose ulcers. Said compositions comprise vancomycin, gentamicin, amikacin, fluconazole, ciprofloxacin and metronidazole or its corresponding salts and an hypertonic amount of sodium chloride in a suitable polar and aprotic or protic acidic as pharmaceutical carrier. There is further disclosed a methods for treating ulcers in mammals using the disclosed compositions.

20 Claims, No Drawings

COMPOSITION AND METHOD FOR TREATMENT OF ULCERS

FIELD OF THE INVENTION

This invention is directed to an acidic, aqueous saline composition comprising particular known organic compounds and a method of treating infected external ulcers using said composition.

BACKGROUND OF THE INVENTION

As it is already very well-known, diabetes mellitus, or simply diabetes is a chronic disease that takes place when the pancreas is no longer able to produce insulin, or when the body cannot make good use of the insulin it produces. Insulin is a hormone made or produced by the pancreas, which is required and essential in the process of breaking down the glucose provided by the food we eat once it passes from the blood stream into the cells in the body in order to produce energy. Thus, whenever a body is not able to produce insulin or to use it effectively, the levels of glucose in the blood stream raises. Said high levels of glucose in the blood are associated with damage to the body and failure of various organs and tissues that may causes death of the patient.

The International Diabetes Federation (IDF) provides valuable data concerning different aspects and effects of people suffering diabetes worldwide. For the year 2014 have been reported that (1) worldwide there were 387 million people with diabetes and it is estimated that by 2035, such amount will rise to 592 million; (2) diabetes has caused 4.9 million deaths in 2014 and every seven seconds a person dies from diabetes; (3) that the economic cost of health expenditure is extremely high, being informed for in 612 billion of dollars and (4) 77% of people with diabetes live in low- and middle-income countries.

A high percent of people with diabetes eventually develops external sores or ulcers in the skin, particularly in their foot or legs, mainly due to two high risk factors, which are very common in diabetes patients: nerve damage, also known as neuropathy and blood vessels damage caused by peripheral vascular disease. Said high risk factors are conditions found more often in people with diabetes.

Once an ulcer is formed, it is very common that it becomes inflamed and infected by microorganisms. If not properly attended, such infection may expand and deepens in the affected area. In some instances, the infection may extend to the bone, causing osteomyelitis. Amputation of the affected foot or leg is regularly necessary due to several medical factors, such as persistency of the infection, chronic state of the ulcer, poor or inefficient antibiotic treatment, and lack of proper medication. Furthermore, social and economic conditions of the patient have been pointed out as factors having a positive impact in the progression of the ulcers due to the lack of resources to pay for proper, efficient and fast medical care. Such conditions may result in the amputation of the affected body area.

Once a patient suffers an amputation, his life quality is highly decreased as well as his independence and his ability to work, thus producing negative consequences in his psychological, economic and social aspects and reducing his life expectancy drastically.

An essential part of the treatment of infected ulcers is the use of topical anti infection therapy with the intention to eliminate pathogens or microorganisms, to reduce inflammation and to promote the wound healing process. In most cases, the topical anti infection active agent is delivered by means of pharmaceutical viscous carries that usually get sticks to the bandage or the external skin of the ulcer and that does not reduce the itching, inflammation and pain associated with the area of the ulcer.

Thus, there is a need for an effective treatment of infected ulcers particularly in diabetic patients.

SUMMARY OF THE INVENTION

During the medical practice of treatment ulcers of diabetic patients, the Inventor has surprisingly discovered an acidic and high saline composition, which is highly effective when used as a topical anti-infected agent. Said composition comprises pharmaceutically active amounts of the following well known chemical compounds: vancomycin, gentamicin, amikacin, fluconazole, ciprofloxacin and metronidazole and/or its respective salts.

Vancomycin is a well-known antibiotic useful for the treatment of a number of bacterial infections. It is of the glycopeptide antibiotic class and is effective mostly against Gram-positive bacteria. It was first isolated in 1953 and described in U.S. Pat. No. 3,076,099 issued Dec. 4, 1962 to Eli Lilly and Co.

Gentamicin is an aminoglycoside antibiotic composed of a mixture of related gentamicin components and fractions and is used to treat many types of bacterial infections, particularly those caused by Gram-negative organisms. It was disclosed in U.S. Pat. No. 3,915,955 issued Oct. 28, 1875 to Schering Co. Similarly, amikacin is another aminoglycoside antibioticis used to treat different types of bacterial infections, particularly infections caused by multi-drug resistant bacteria. It has been disclosed in U.S. Pat. No. 3,781,268 issued Dec. 25, 1973 to Bristol-Myers Co.

Fluconazole is an antifungal medication, usually administered by mouth or intravenously. It is useful in the treatment of a variety of fungal infections and is disclosed, for instance in U.S. Pat. No. 4,416,682 issued Nov. 22, 1983 to Imperial Chemical Industries, PLC.

Ciprofloxacin is an antibiotic useful for the treatment of a number of bacterial infections, thus having a broad spectrum activity, including Gram-negative and Gram-positive bacterial pathogens. It is disclosed as the monohydrate hydrochloride salt in U.S. Pat. No. 4,670,444, issued Jun. 2, 1987 to Bayer Ak.

Metronidazole is a nitro imidazole antibiotic used particularly for treating infections of anaerobic bacteria and protozoa. It is disclosed in U.S. Pat. No. 2,944,061 issued on Jul. 5, 1960 to Jacobs et al.

OBJECTS OF THE INVENTION

It is an object of the invention to provide a composition comprising pharmaceutically accepted amounts of compounds vancomycin, gentamicin, amikacin, fluconazole, ciprofloxacin and metronidazole in an acidic saline hypertonic media. It is another object of the invention to provide a method of treating ulcers in mammals, which comprises topically administrating to such mammals an effective amount of the composition comprising pharmaceutically accepted amounts of compounds vancomycin, gentamicin, amikacin, fluconazole, ciprofloxacin and metronidazole in an acidic saline hypertonic media.

Another object of the invention is to provide a method of treating ulcers in mammals suffering from diabetes ulcers and other types of ulcers, which comprises topically administrating to the ulcer in such mammals an effective amount of the composition comprising pharmaceutically accepted amounts of compounds vancomycin, gentamicin, amikacin, fluconazole, ciprofloxacin and metronidazole in an acidic saline hypertonic media.

DESCRIPTION OF THE INVENTION

The instant invention is directed to a composition that has been surprisingly found to be highly effective and efficient in the treatment of infected ulcers, particularly infected ulcers in patients already diagnosed with diabetes. Similarly, the composition herein described has also been found effective in the treatment of other external infected ulcers or wounds such as varicose ulcers.

For the purpose of the instant application, an infected ulcer means diabetic foot ulcer or any other external, open skin ulcer that have been colonized with microorganisms creating an infection or a colony of pathogens that may comprises different types of bacteria or any other mammal pathogens.

The term "mammal" refers to humans and to other animals, vertebrates and non-vertebrates.

The term "chemical or pharmaceutical composition" or "chemical or pharmaceutical compositions", herein used in singular or plural refers to or comprises any composition comprising the compounds and conditions in the particular range disclosed in the instant application. Similarly, the word "method" or "methods" as used in this application refers to or comprises any method for treating ulcers in mammals by administering to a subject suffering from said ulcers any of the chemical or pharmaceutical compositions within the scope of the compositions herein disclosed.

Topical administration as required for the instant invention is refers to a direct contact of the herein disclosed composition with the exterior area of the ulcer or wound, preferably by spraying the composition directly to the infected ulcer.

Compositions

The chemical composition is obtained as a clear and odorless liquid solution having a pH in a range of 3.5 to 6.5, preferably in a range of 4.0 to 6.0 and even more preferably of 5.0. It comprises pharmaceutical amounts of compounds vancomycin, gentamicin, amikacin, fluconazole, ciprofloxacin and metronidazole dissolved in a suitable aqueous acidic protic or aprotic pharmaceutical carrier, and to which sodium chloride is added as a hypertonic saline solution.

The suitable pharmaceutical amounts for each one of the compounds in the herein disclosed composition may be varied, modified or adjusted widely, depending particularly of the severity of the infection to be treated. The preferable amount for each one of the compounds in the disclosed composition is in the following ranges, expressed in volume weight per volume percent, (weight/volume % or w/v %) expressed in (g/ml) % and calculated based upon the total weight of the compound in the total volume of the composition, are:

| Compound | Low range w/v % | High range w/v % |
|---|---|---|
| Vancomycin | 0.32 | 0.52 |
| Gentamicin | 0.03 | 0.23 |
| Amikacin | 0.73 | 0.93 |
| Fluconazole | 0.01 | 0.04 |
| Ciprofloxacin | 0.01 | 0.04 |

Regarding the hypertonic saline solution as used in the preparation of the disclosed composition, it refers to a hypertonic sodium chloride solution in deionized water, which comprises a higher concentration of both sodium and chloride than the amounts of sodium and chloride typically contained in the cells to which the solution is administered. The composition disclosed embrace any potential hypertonic solution, since the concentration of sodium chloride may be varied, modified or adjusted widely, depending particularly of the severity of the infection to be treated. Generally, the amount of sodium chloride in the resulting composition may be preferably in a range of 2 to 5 weight per volume of sodium chloride and even more preferable in a range of 3 to 4 weight per volume of sodium chloride.

The composition may be prepared by standard methods known in the art wherein the compounds vancomycin, gentamicin, amikacin, fluconazole, ciprofloxacin and metronidazole are dissolved in a suitable polar and aprotic or protic pharmaceutical carrier, such as acidic deionized water, dimethyl sulfoxide (DMSO), ethyl alcohol or mixture thereof.

In one of the preferred embodiments of the invention, the pharmaceutical carrier is acidic deionized water. Optionally, it may be acidic deionized water with minimum amounts of ethanol or DMSO used to increase or facilitate the solubility of some of the organic compounds in the aqueous acidic media. Once the solution vancomycin, gentamicin, amikacin, fluconazole, ciprofloxacin and metronidazole are dissolved in the pharmaceutical carrier, to the resulting mixture is further added sodium chloride, preferably by adding to it the corresponding volume of saline hypertonic solution and the pH of the resulting solution is adjusted to the preferably range of 3.5 to 6.5, preferably in a range of 4.0 to 6.0 and even more preferably of 5.0 without the addition of any thickening agents, since it is highly desirable that the composition has a low viscosity or non-thicknesses consistency and thus it may be freely dispersed.

In a prefer method for preparing the composition, pharmaceutical amounts of compounds vancomycin, gentamicin, amikacin and metronidazole are readily dissolved in a minimum amount of deionized water. Pharmaceutical amount of fluconazole may be dissolved in a minimum volume of deionized water. Alternatively, fluconazole may be dissolved in minimum amounts of aqueous acidic ethanol or minimum amounts of dimethyl sulfoxide (DMSO) or aqueous mixtures of ethanol and/or DMSO. After dissolution is achieved, the resulting mixture is added to the solution containing compounds vancomycin, gentamicin, amikacin and metronidazole and the pH of the resulting mixture is adjusted to preferably range disclosed above. Regarding ciprofloxacin, since it's almost insoluble in water and alcohol and its solubility extremely depends on the pH of the dissolving media, a pharmaceutical amount of the corresponding hydrochloric salt of said compound is dissolved in the minimum amount of water and the resulting solution is then combined with the solution containing the others compounds previously dissolved to which the hypertonic saline solution is added in order to provide the composition.

Alternatively, in an even more preferably process, the pharmaceutical amount of the hydrochloric salt or any other suitable organic salts of each one of the organic compounds required in the composition and previously identified may be dissolved in minimum acidic deionized water. The dissolution of such salts may be made independently, thus providing independent solutions that are later combined or some of the compounds may be dissolved in any possible combination and then combined. Alternatively, the corresponding organic salts may be dissolved at once in deionized water. To the resulting solution obtained in any of the potential processes is then added sodium chloride as the hypertonic saline solution in order to provide the required composition after the pH has been adjusted within the indicated or desired range.

On at even alternative manner, the free base of the organic compounds may be suspended in deionized water and induce into solution by means of adding aqueous acidic solution preferably with a pH in a range of 3.5 to 6.5, preferably in a range of 4.0 to 6.0 and even more preferably 5.0. To said solution, sodium chloride is added as a hypertonic saline solution and combined, thus resulting in the final composition as a clear, homogeneous, odorless and totally transparent aqueous composition.

Similarly, the in another embodiment of the invention, pharmaceutical amounts of the corresponding organic salts of vancomycin, gentamicin, amikacin, fluconazole, ciprofloxacin and metronidazole, preferably the corresponding hydrochloric salts, are dissolved in deionized water at a pH range of 4.5 to 5.5 and to the resulting mixture is added the corresponding amount of sodium chloride as a hypertonic saline solution in order to provide a clear homogeneous composition according to the instant invention.

Method of Topical Treatment of Ulcers

The herein method of treating ulcers comprises administering a composition according to of the invention to the ulcer of a mammal topically. In operational terms, diabetic patients suffering from infected, open ulcers are first evaluated by conventional means. The ulcer area is evaluated in terms of the conditions presented such as inflammation or swelling, color of the affected area or redness, secretions, signs of itching and tingling and burning sensations, pain and fever, condition of the inner skin and surrounding skin. The patient is treated with conventional antibiotic therapy while samples of the tissue and or secretions of the ulcer are subjected to microbiological identification tests in order to characterized and/or identify pathogens and properly treat the patient with the right antibiotic therapy orally or systemically, whenever it is necessary.

Regarding the topical treatment of the ulcer with the herein disclosed composition, the ulcer area is first treated by spraying the composition thoroughly over the said area. Then, the ulcer area is covered with sterile gauze previously soaked up with the disclosed composition. Dry sterile gauzes are then used to cover the first gauze layer containing the composition and are further secured with adhesive bands in order to complete the ulcer area dressing.

The dressing is removed from the ulcer area at a given time, preferably in a period of every twenty four (24) hours, and the treated area is macroscopically evaluated again. The ulcer area is then treated with the composition in the same manner as initially explained and indicated above until the process of healing takes place. The healing time depends on the conditions of the ulcer; surprisingly, ulcers from simple to even those showing osteomyelitis have been treated successfully with the herein disclosed composition and method.

At the initial treatment with the composition, it is observed that after near ten (10) minutes, patient lacks the itching, pain and burning sensations in the ulcer area, thus avoiding the need of the patient to scratches the treated area. Since the composition is odorless, it does not produce bad odors and it facilitates the identification of bad odors from the ulcer itself. Similarly, since it is colorless, there is no change in color in the treated area due to its application, facilitating the color changes of the treated area due to the ulcer condition. Within an average of three (3) days under the topical treatment with the composition there is a significant decrease in exudative secretions from the ulcer, as well as a reduction of the bad odor and the swelling of the affected area. After an average of five (5) days, the redness of the skin disappears and the patient gains mobility of the affected body extension. Eventually, it is observed an emerging new vascular red or angiogenesis along with granulation indicators and new tissue until the closing or healing of the wound or ulcer is achieved. The herein disclosed method presents the advantage that patients may be treated in outpatient's bases, decreasing the hospital's costs. Furthermore, is has been found highly efficient in healing ulcers of different grades of complexities, thus reducing the time of healing and also reducing the need for performing amputations.

The method has also been found successful in the treatment of non-diabetic ulcers such as varicose ulcers by topically administering to the ulcers patients the herein disclosed composition. In such ulcers, a clinical analysis of the ulcers content and tissues is carried out in order to properly identify the presence of pathogens in the ulcer and provided to the patient with the appropriate antibiotic therapy along with the treatment of the ulcer with the composition in a similar manner already explain above for the diabetic ulcers.

Compositions within the limitations herein described are prepared easily and are relatively inexpensive, easy to applied topically and provide a fast relief of itching and inflammation, thus reducing the need of the patient of scratching the affected ulcer area. The compositions also present the advantages that are prepared with chemicals well known in the art that have been approved for medical use and are prepared by well-established pharmaceutical methods. Due to its highly effective activity, the compositions herein disclosed reduce ulcers treatment time and the costs associated with such conditions such as hospital stays, expensive treatments and the like.

What is claimed is:

1. A pharmaceutical composition for topically treating an infected ulcer in a mammal, said composition comprising:
    (a) vancomycin, gentamicin, amikacin, fluconazole, ciprofloxacin, and metronidazole or pharmaceutically acceptable salts thereof;
    (b) a hypertonic amount of sodium chloride; and
    (c) a suitable polar and aprotic or protic acidic pharmaceutical carrier.

2. The pharmaceutical composition of claim 1, wherein the composition comprises:
    (a) about 0.32% to about 0.52% weight per volume of vancomycin upon the total volume of the composition;
    (b) about 0.03% to about 0.23% weight per volume of gentamicin upon the total volume of the composition;
    (c) about 0.73% to about 0.93% weight per volume of amikacin upon the total volume of the composition; (d) about 0.01% to about 0.04% weight per volume of fluconazole upon the total volume of the composition;
    (e) about 0.01% to about 0.04% weight per volume of ciprofloxacin upon the total volume of the composition;
    (f) about 0.02% to about 0.06% weight per volume of metronidazole upon the total volume of the composition; (g) about 2.0% to about 5.0% weight per volume of sodium chloride; and (h) an amount of the suitable polar and aprotic or protic acidic pharmaceutical carrier sufficient to provide a final pH of the composition in a range of 3.5 to 6.5.

3. The pharmaceutical composition of claim 2, wherein the pH of the composition is in the range of 4.0 to 6.0.

4. The pharmaceutical composition of claim 2, wherein the pH of the composition is 5.0.

5. The pharmaceutical composition of claim 2, wherein the suitable polar and aprotic or protic acidic pharmaceutical carrier is selected from acidic deionized water, dimethyl sulfoxide, ethyl alcohol or a mixture thereof.

6. The pharmaceutical composition of claim 5, wherein the suitable polar and aprotic or protic acidic pharmaceutical carrier is acidic deionized water.

7. The pharmaceutical composition of claim 5, wherein the suitable polar and aprotic or protic acidic pharmaceutical carrier is a mixture of acidic deionized water and ethyl alcohol.

8. The pharmaceutical composition of claim 5, wherein the suitable polar and aprotic or protic acidic pharmaceutical carrier is a mixture of acidic deionized water and dimethyl sulfoxide.

9. The pharmaceutical composition of claim 5, wherein the suitable polar and aprotic or protic acidic pharmaceutical carrier is a mixture of acidic deionized water, dimethyl sulfoxide and ethyl alcohol.

10. The pharmaceutical composition as recited in claim 2, wherein the range of sodium chloride in the claimed composition is about 3.0% to about 4.0% weight per volume.

11. A method for topically treating an infected ulcer in a mammal, the method comprising applying a pharmaceutically effective amount of the composition of claim 1 over the infected ulcer.

12. The method of claim 11, wherein the pharmaceutical composition is applied to the infected ulcer by spaying said composition.

13. The method of claim 11, wherein the infected ulcer is a diabetic patient ulcer.

14. The method of claim 13, wherein the infected ulcer is a diabetic foot ulcer.

15. The method of claim 11, wherein the infected ulcer is a varicose ulcer.

16. A method for preparing the pharmaceutical composition for topically treating an infected ulcer in a mammal according to claim 1, said method comprising dissolving a therapeutically effective amount of vancomycin, gentamicin, amikacin, fluconazole, ciprofloxacin, and metronidazole or pharmaceutically acceptable salts thereof and a hypertonic amount of sodium chloride in a suitable polar and aprotic or protic acidic pharmaceutical carrier.

17. The method for preparing the pharmaceutical composition according to claim 16, wherein the suitable polar and aprotic or protic acidic pharmaceutical carrier is selected from acidic deionized water, dimethyl sulfoxide, ethyl alcohol or a mixture thereof.

18. The method for preparing the pharmaceutical composition according to claim 17, comprising the steps of:
a) preparing a hypertonic solution of sodium chloride by dissolving a hypertonic amount of sodium chloride in deionized water;
b) preparing individual solutions of vancomycin, gentamicin, amikacin, and metronidazole or its salts thereof by dissolving therapeutically effective amounts of each one of said compounds in deionized water;
c) preparing a solution of fluconazole by dissolving a therapeutically effective amount of fluconazole in dimethyl sulfoxide;
d) preparing a solution of ciprofloxacin or a pharmaceutical acceptable salt thereof by dissolving a therapeutically effective amount of ciprofloxacin or a pharmaceutical acceptable salt thereof in acidic aqueous solution;
e) combining a therapeutically effective volumetric amount of each one of the individual solutions or aliquots produced in the steps (a), (b), (c) and (d); and
f) adding acidic deionized water to adjust the pH of the resulting composition to the desired pH range.

19. The method for preparing the pharmaceutical composition according to claim 17, comprising the steps of:
a) preparing a hypertonic solution of sodium chloride by dissolving a hypertonic amount of sodium chloride in deionized water;
b) preparing individual solutions of vancomycin, gentamicin, amikacin, and metronidazole or its salts thereof by dissolving therapeutically effective amounts of each one of said compounds in deionized water;
c) preparing a solution of fluconazole by dissolving a therapeutically effective amount of fluconazole in ethanol;
d) preparing a solution of ciprofloxacin or a pharmaceutical acceptable salt thereof by dissolving a therapeutically effective amount of ciprofloxacin or a pharmaceutical acceptable salt thereof in acidic aqueous solution;
e) combining the individual solutions produced in the steps (a), (b), (c) and (d); and
f) adding acidic deionized water to adjust the pH of the resulting composition to the desired pH range.

20. The method for preparing the pharmaceutical composition according to claim 17, comprising the steps of:
a) preparing a hypertonic solution of sodium chloride by dissolving a hypertonic amount of sodium chloride in deionized water;
b) preparing individual solutions of vancomycin, gentamicin, amikacin, and metronidazole fluconazole and ciprofloxacin or its salts thereof by dissolving therapeutically effective amounts of each one of said compounds in a mixture of acidic deionized water, dimethyl sulfoxide and ethanol;
c) combining the solutions produced in the steps (a) and (b); and
d) adding acidic deionized water to adjust the pH of the resulting composition to the desired pH range.

* * * * *